United States Patent [19]

Griffin et al.

[11] Patent Number: 5,230,897
[45] Date of Patent: Jul. 27, 1993

[54] TRANSDERMAL PENTAMIDINE

[75] Inventors: Martin J. Griffin, McHenry; Tugrul T. Kararli, Skokie; Stanley C. Penzotti, Jr., Green Oaks; Rachelle M. Rydzik, Northbrook; Cynthia M. Schmidt, Gurnee, all of Ill.

[73] Assignee: G. D. Searle & Co., Chicago, Ill.

[21] Appl. No.: 785,854

[22] Filed: Oct. 31, 1991

[51] Int. Cl.$^5$ .............................. A61F 13/00
[52] U.S. Cl. ............................ 424/449; 514/637; 514/946; 514/948; 514/772
[58] Field of Search ............... 514/946, 947; 424/447, 424/448, 449

[56] References Cited

U.S. PATENT DOCUMENTS

| | | | |
|---|---|---|---|
| 4,440,777 | 4/1984 | Zupan | 424/274 |
| 4,722,941 | 2/1988 | Eckert et al. | 514/784 |
| 4,820,525 | 4/1989 | Leonard | 424/486 |
| 4,853,416 | 8/1989 | Anaebonam et al. | 514/636 |
| 4,863,970 | 9/1989 | Patel et al. | 514/784 |
| 4,931,283 | 6/1990 | Tsuk | 424/429 |
| 4,933,184 | 6/1990 | Tsuk | 424/449 |
| 4,956,355 | 9/1990 | Prendergast | 514/178 |

FOREIGN PATENT DOCUMENTS

351897  1/1990  European Pat. Off.

Primary Examiner—Thurman K. Page
Assistant Examiner—Leon R. Horne
Attorney, Agent, or Firm—Cynthia S. Kovacevic; Paul D. Matukaitis; Roger A. Williams

[57] ABSTRACT

Pharmaceutical compositions and transdermal patches comprised of pentamidine and a penetration enhancing amount of a terpene selected from the group consisting of menthol, carvone, carveol, dihydrocarveol, dihydrocarvone, neomenthol, isopulegol, terpene-4-ol, menthone, pulegol, camphor, geraniol, α-terpineol, citral, linalol, carvacrol, thymol and anethole are disclosed for delivery of a therapeutically effective amount of pentamidine or its pharmaceutically acceptable salts.

30 Claims, 3 Drawing Sheets

TRANSDERMAL PENTAMIDINE

FIELD OF THE INVENTION

The present invention is for pharmaceutical compositions and patches for transdermal delivery of pentamidine which use a penetration enhancer to facilitate the percutaneous and transepidermal delivery of pentamidine and its pharmaceutically acceptable salts.

BACKGROUND OF THE INVENTION 4,4'-[1,5-Pentanediylbis(oxy)]bisbenzenecarboximidamide, generically known as pentamidine, is known to be an effective anti-protozoal and fungicidal agent, particularly it has been used in the treatment of trypanosomiasis (sleeping sickness). More recently, since the advent of the AIDS epidemic (Acquired Immune Deficiency Syndrome) pentamidine has been used in the treatment of pneumocystis carinii pneumonia which is often contracted by AIDS and ARC (AIDS Related Complex) patients. Additionally, pentamidine is used in the treatment and prophylaxis of leishmaniasis.

Initially pentamidine was administered either intravenously or by intramuscular injection. More recently investigators have found that an aqueous solution of pentamidine administered by inhalation is useful for the prophylactic or remedial treatment of pneumocystis carinii pneumonia. (U.S. Pat. No. 4,853,416 issued Aug. 1, 1989).

The present invention results in a new form of administration of pentamidine and its pharmaceutically acceptable salts, by formulating it into a transdermal pharmaceutical composition or a pharmaceutical composition comprised within a transdermal patch together with a penetration enhancer to achieve blood levels of pentamidine which are effective in the treatment and prophylaxis of protozoal and fungal diseases such as pneumocystis carinii pneumonia.

Transdermal delivery of pentamidine offers advantages over the other methods of delivery of pentamidine. An advantage is the ease of application and removal of a transdermal formulation over the 'complex, device assisted aerosol delivery and over the intravenous or intramuscular delivery. This convenience of use offers the benefit of a lifestyle uninterrupted by hospital visits, which are needed when administering pentamidine by other known methods. Administration by IV or intramuscular delivery has certain disadvantages of inadvertent needle sticks that are especially undesirable when working with AIDS or ARC patients. Needle sticks have also been associated with the risk of secondary systemic infections. Transdermal delivery does provide the ability to deliver drugs directly to general circulation. Transdermal delivery of pentamidine is also advantageous in that it can be used in pediatric age groups, whereas aerosol administration of pentamidine cannot be used. Transdermal delivery of pentamidine also avoids the disadvantage of having chronic exposure of health care workers to pentamidine which is a risk associated with aerosol delivery.

Recognizing that the outer layer of the skin, the epidermis, protects the area under the skin from penetration of foreign chemicals, various enhancing agents have been used to deliver drugs transdermally. Substances that help promote drug diffusion through the stratum corneum and epidermis are referred to as skin-penetration enhancers, accelerants, adjuvants and sorption promoters. B. Idson, *Cosmetics & Toiletries*, 95, 59 (1980) states that the factors affecting drug penetration and consequently, in most cases, effectiveness, are complex. The vehicle that provides ideal conditions for one drug may prove unsatisfactory for another.

Various penetration enhancers are known to be useful in transdermal drug delivery. U.S. Pat. No. 4,863,970, U.S. Pat. No. 4,722,941, U.S. Pat. No. 4,931,283 and EP 351,897 disclose some representative penetration enhancers used in transdermal compositions and for topical administration.

SUMMARY OF THE INVENTION

The present invention provides a pharmaceutical formulation in the form of a transdermal delivery system comprised of pentamidine or its pharmaceutically acceptable salts and a penetration enhancer. The present inventors have determined that various terpenes, selected from the group consisting of menthol, carveol, dihydrocarvone, dihydrocarveol, carvone, neomenthol, isopulegol, terpene-4-ol, menthone, linalol, carvacrol, thymol, camphor, pulegone, geraniol, α-terpineol, citral and t-anethole are effective penetration enhancers for delivery of pentamidine transdermally.

It is the primary object of this invention to provide a pharmaceutical composition for transdermal delivery of pentamidine and a further object of this invention is to provide a transdermal patch for effective transdermal delivery of the pentamidine composition.

Another object of this invention is to provide a percutaneous penetration enhancer for use in the transdermal delivery of pentamidine.

BRIEF DESCRIPTION OF THE DRAWING

FIG. 1 illustrates a cross sectional view of a transdermal patch that is designed to be placed on skin for transdermal delivery of pentamidine.

FIG. 2 is a bottom plan schematic view of the embodiment of the invention illustrated in FIG. 1.

FIG. 3 illustrates a template used for topical administration of a transdermal pentamidine formulation.

FIG. 4 illustrates a sectional schematic view of a second embodiment of a transdermal patch for the transdermal delivery of pentamidine.

FIG. 5 illustrates a sectional schematic view of a third embodiment of a transdermal patch.

FIG. 6 is a graphical representation of the blood plasma level of pentamidine after intravenous dosing.

FIG. 7 is a graphical representation of the blood plasma level of pentamidine after transdermal dosing.

FIG. 8 is a graphical representation of the results of pentamidine transport across nude mice skin in vitro.

DETAILED DESCRIPTION OF THE INVENTION

This invention encompasses transdermal compositions of pentamidine as previously described. Pentamidine has the structural formula I

(I)

The term "pharmaceutically acceptable salts" refers to non-toxic salts formed by acid-base reactions. Typical pharmaceutical salts are listed in S. M. Berge et al., "Pharmaceutical Salts", *J. Pharm. Sci.*, 66:1–19 (1977). All of the pharmaceutically acceptable salts are prepared by methods commonly used and known by those of ordinary skill in the art. The most preferred pentamidine salt is pentamidine isethionate.

The term "composition" as used herein means a product which results from the mixing or combining of more than one element or ingredient.

The term "pharmaceutically-acceptable carrier" as used herein means a pharmaceutically acceptable material, composition or vehicle, such as a liquid or solid filler, diluent, excipient, or solvent involved in carrying or transporting a chemical agent from one organ or portion of the body to another organ or portion of the body.

The term "terpene" as used herein means any of the terpenes selected from: menthol, carveol, carvone, citral, dihydrocarveol, dihydrocarvone, neomenthol, isopulegol, terpene-4-ol, menthone, linalol, carvacrol, thymol, pulegone, camphor, geraniol, α-terpineol, and t-anethole, including their specific isomers and racemic mixtures.

The term "transdermal delivery" as used herein means administration of the pharmaceutical composition topically to the skin wherein the active ingredient, pentamidine or its pharmaceutically acceptable salts, will be percutaneously delivered in a therapeutically effective amount.

The term "transdermal patch" as used herein means a skin patch to be applied to the patient's skin containing the pharmaceutical composition. The technology for constructing transdermal patches is well known in the pharmaceutical art.

The terms "backing layer" and "reservoir" as used herein are components of the transdermal patch. Suitable materials and designs are well known in the transdermal drug delivery art. See for example D. Hsieh, "Multiple Lamination for Transdermal Patches," *Controlled Release Systems Fabrication Technology*, Vol. 1, pp. 167-188, 1988.

The term "penetration enhancers" as used herein means compounds which enhance the percutaneous absorption of drugs. Selection of an effective penetration enhancer for a particular drug must be experimentally deduced. A penetration enhancer which works for one drug will not necessarily work for every other drug B. Idson, *Cosmetics & Toiletries*, 95, 59 (1980).

By virtue of its activity as an anti-protozoal and an antipneumocystis, pentamidine and its pharmaceutically acceptable salts are useful in the treatment and prophylaxis of pneumocystis carinii pneumonia.

In the present invention pentamidine or its pharmaceutically acceptable salts are administered transdermally by topical application of a pentamidine composition to the skin. More preferably pentamidine can be administered in the form of a gel and covered with an occlusive bandage or it can be administered using a transdermal patch in which the pentamidine is incorporated. The pharmaceutical compositions and patches of the present invention can administer pentamidine or its pharmaceutically acceptable salts in admixture with a terpene penetration enhancer and suitable pharmaceutical diluents, carriers and excipients such as gelling agents, emollients (i.e., allantoin), and preservatives (i.e., parabens). Various compounds with acidic pHs can be added to the composition as stabilizer. Preferably the pentamidine is administered in admixture with the penetration enhancer menthol.

A preferred solvent system for delivery of pentamidine includes an isopropyl alcohol (IPA) and water mixture wherein the IPA can be present in the range of 20%–60% w/v and the water can be present in the range of 80–40% w/v. Although lesser or greater concentration of isopropyl alcohol could be used it is within these ranges that all components of the composition are soluble at effective concentrations. Alternatively, a lower vapor pressure solvent system, such a 50% propylene glycol and 50% water system can be used.

The practicality of administering a given drug percutaneously on a continuous basis depends upon the concentration of drug in the blood that is required to provide the desired pharmacologic effect, the degree to which the skin is permeable to the drug, and the amount of skin surface area that is available for drug administration.

The skin surface area which is available for drug administration, while theoretically being unlimited, is, for practical reasons, typically confined to a range of from about 1 square centimeters to about 100 square centimeters. With the available skin surface area fixed within this range, the matter then narrows as to whether sufficient drug will pass through the defined skin surface area to provide the desired therapy. If it will, then it may not be difficult to effectively administer the drug percutaneously. If, however, the inherent permeability of the skin to the drug is so high or so low that too much or too little drug will pass through that area of skin, then the rate of administration of the drug to the skin must be controlled, or the permeability of the skin to the drug must be increased, as the case may be, to make percutaneous administration practical.

The present invention involves a drug delivery system in which the percutaneous administration of the drug is enhanced by the presence of a penetration enhancer.

In order for a compound to be useful as a percutaneous penetration enhancer the compound must meet a number of different requirements. Firstly, the compound must be a dermatologically acceptable compound which when used topically on the skin does not cause adverse side effects. Secondly, the compound must be compatible with the active ingredient in the transdermal delivery system. Thirdly, it is preferable for the compound to be safe and efficacious for use on humans, preferably approved or approvable by the Food and Drug Administration of the United States. Further, the compound must increase the transdermal rate of delivery of the pharmaceutically active drug.

It has been found herein that for transdermal delivery of pentamidine a penetration enhancer is desirable. Suitable penetration enhancers for pentamidine and its pharmaceutically acceptable salts are certain compounds generally classified as terpenes. Not all terpenes were found to be active penetration enhancers for pentamidine. Terpene compounds that are useful as penetration enhancers for pentamidine include any terpene compound selected from the group consisting of menthol, carvone, dihydrocarveol, dihydrocarvone, carveol, neomenthol, isopulegol, terpene-4-ol, menthone, linalol, carvacrol, thymol, camphor, pulegol, geraniol, α-terpineol, citral and t-anethole. A preferred penetration enhancer is menthol.

In treatment or prophylaxis of pneumocystis carinii pneumonia, use of a non-toxic but therapeutically effective amount of pentamidine or its pharmaceutically acceptable salts is employed. The dose regimen for preventing or treating pneumocystis carinii pneumonia with pentamidine or its pharmaceutically acceptable salts is selected in accordance with a variety of factors including the type, age, weight, sex and medical condition of the patient. A physician of ordinary skill can readily determine and prescribe an effective amount of the drug required to prevent or treat the progress of condition.

In order to achieve a therapeutic effect of pentamidine given parenterally, in a human adult suffering from pneumocystis carinii pneumonia which is treatable and preventable with pentamidine, a dose of 3–4 mg/kg/day of pentamidine is administered for 2-3 weeks. For prophylaxis similar doses are given once a month. Pentamidine administered transdermally achieves similar plasma concentrations (measured as AUC - area under curve) as the parenteral. In the preferred embodiment of the present invention pentamidine is administered in an amount of 3–4 mg/kg once daily. In a preferred embodiment of the present invention pentamidine is delivered to an adult patient in an amount of 300 mg daily. These doses were selected in order to achieve pentamidine blood levels equivalent to that achieved with parenteral dosing. The required dose of active ingredient to be administered will vary with, amongst other factors, the severity of the condition being treated, and will depend on whether the treatment is remedial or prophylactic.

In order to administer the dose set out above the concentration of pentamidine in the composition can be from about 5% to about 30% w/w. The concentration of pentamidine, is however, preferably from about 15% to about 25%, and more preferably from about 20% to about 25%.

The concentration of the terpene penetration enhancer in the composition can be from about 0.1% to about 10% w/w. The concentration of the terpene is, however, preferably from about 2% to about 8% and more preferably from about 3% to about 5%. Although preferred concentrations of terpenes are stated above, it is to be understood that concentration of the terpene greater than 10% will deliver the pentamidine transdermally but that in the preferred embodiments effective transdermal delivery of pentamidine must be balanced with skin irritation and solubility.

While concentrations of pentamidine and penetration enhancers are given herein in ranges with a maximum and a minimum concentration, amounts greater than or less than such limits can be used without varying from the invention as is understood by one having skill in the art.

The amount of pentamidine and penetration enhancer incorporated in the reservoirs or matrix of the transdermal patches of the invention to obtain the desired therapeutic effect can vary depending upon the desired dose of the pentamidine, the length of time the patch is to remain on the skin of the patient and the area and thickness of the patch. Patient plasma concentrations of the pentamidine can thus be adjusted by varying the concentration of the pentamidine in the patch, the length of time the patch is to remain on the skin of the patient or the patch size.

The effective rate of release of the pentamidine from the patches of the invention to the skin of a patient can be in the range of from about 1 to about 250 milligrams of active agent per square centimeter of skin per day (mg.cm$^{-2}$. day$^{-1}$). A more preferred range is from about 50 to about 100 milligrams of active agent per square centimeter of skin per day. The exact amount depends on the desired dose of the active agent and whether the treatment is remedial or prophylactic.

Those skilled in the art can readily determine the rate of permeation of active drug ingredient through a particular matrix material, and through selected combinations of matrix materials, to be employed in a patch of the invention. Standard techniques employed for making such determinations are described in the *Encyclopedia of Polymer Science and Technology*, Volumes 5 and 9, Pages 65 to 85 and 795 to 807 (1968), and the references cited therein.

Other excipients and pharmaceutical carriers can be present in the compositions and patches of the present application. An example of an excipient useful as a gelling agent for preparing a topical gel is carboxypolymethylene, commercially available as Carbopol 940. Pharmaceutical carriers which can be used include for example mixtures of isopropanol and water. The parabens are suitable preservatives for use in transdermal pentamidine compositions.

The pharmaceutical compositions of the invention can be made, for example, by slow addition of powdered carboxypolymethylene, commercially available as Carbopol 940, to a stirred solution of pentamidine, terpene and parabens. The solution gels and can be poured into a measuring-dispensing device. The gel can be extruded into sealable gel-tubes or syringes. The gel can be applied to the skin in a measured dose, dependent on the factors discussed above and covered with an occlusive bandage.

Figure 2:
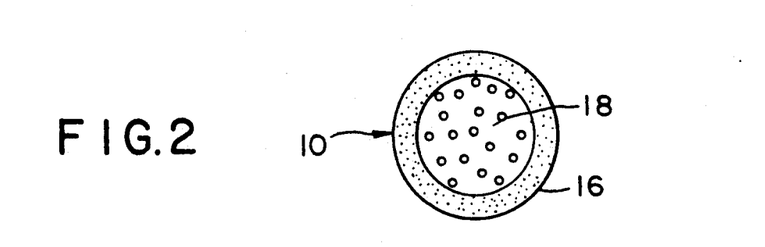

Alternatively, the composition can be incorporated in a transdermal patch for delivery of pentamidine percutaneously. Methodology and design of transdermal patches for drug delivery are well known in the pharmaceutical art.

FIG. 1 illustrates a transdermal patch (10) that is designed to be placed on the skin of the patient. Transdermal patch (10) comprises a backing layer (12); a drug reservoir (18); an adhesive layer (16); and a protective undercoating lamina (19).

The backing layer (12) defines the top (outward surface) of the patch. The backing layer can be made from a material or a combination of materials that is substantially impermeable to the components of the reservoir layer. The backing layer serves as a protective cover for the transdermal patch and keeps the components of the reservoir layer from escaping.

Various occlusive and non-occlusive, flexible and non-flexible backing members can be used as backing layers in the transdermal patches of the present invention. Examples of suitable backing layers for use in the transdermal patches herein include cellophane, cellulose acetate, ethylcellulose, plasticized vinylacetate, vinylchloride copolymers, polyethylene terephthalate, nylon, polyethylene, polypropylene, polyvinylidenechloride, paper, cloth, foam and aluminum foil.

The drug reservoir (18) is immediately below the backing layer (12) and contains the transdermal pentamidine composition. The amount of pentamidine incorporated in the reservoir of the patch of the invention to obtain the desired therapeutic effect can vary depending upon the desired dose of the pentamidine, the length of time the patch is to remain on the skin of the patient and the area and thickness of the patch. Patient blood level concentrations of pentamidine can be adjusted by varying the concentration of the pentamidine in the patch, the length of time the patch is to remain on the skin of the patient or the patch size.

The adhesive layer (16) is affixed to the backing layer (12) surrounding the drug reservoir. This is better illustrated by a view of the patch from the bottom (patient side) as illustrated in FIG. 2. The adhesive layer is the means by which the transdermal patch is affixed to the skin. Contact adhesive compositions can be selected from pressure sensitive adhesives many of which are commonly used on transdermal patches.

Figure 1:
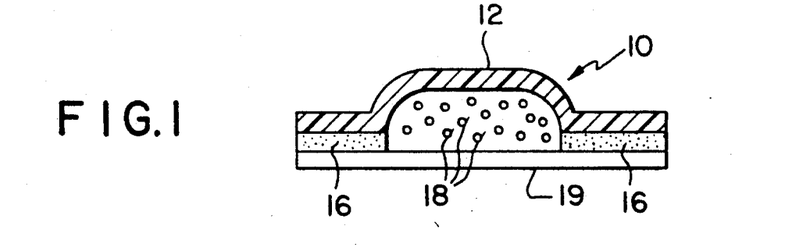

The transdermal patch (10) can include a protective undercoating lamina (19) which covers the entire patient side of the transdermal patch. The protective undercoating lamina protects the pressure sensitive adhesive of the transdermal patch and contains the transdermal composition within the drug reservoir prior to application. Prior to use, the undercoating lamina (19) is pulled away from the adhesive layer (16) and discarded thus exposing the pressure sensitive adhesive and the transdermal composition for application to the skin.

Figure 3:
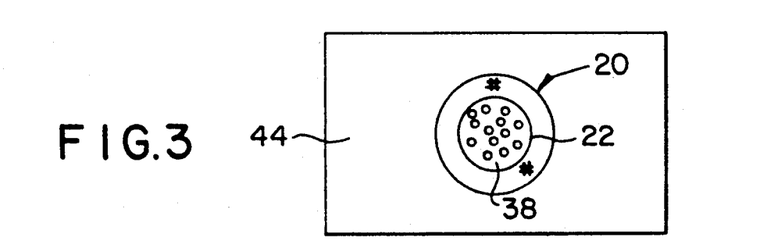
Figure 4:
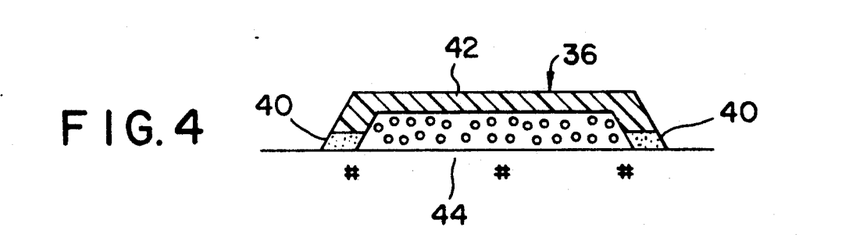

FIG. 3 and FIG. 4 depict another method of using the transdermal pentamidine composition that is the subject of the invention. FIG. 3 illustrates a template (20) which applied to an area of the patient's skin. The inner circumference of the template (20) defines an area (22) of skin to which the transdermal pentamidine composition is to be delivered. The area of skin can be determined by the age, sex, and weight of the patient, whether treatment is prophylactic or remedial, and the blood level of pentamidine to be achieved, discussed supra. A sealable gel tube or syringe containing the transdermal pentamidine composition in a predetermined dose is opened. The dose is determined by the factors discussed above. The transdermal pentamidine composition is applied within the inner circumference of the template. The template is removed from the skin.

FIG. 4 depicts an occlusive covering (36) which is placed over the applied transdermal pentamidine composition and the same area of the patient's skin after the template has been removed. The occlusive covering can include a backing layer (42) and an adhesive layer (40) which have the same properties and are chosen for the same reasons as stated above for the transdermal patch. The adhesive layer can be the same width and circumference as the template. The occlusive covering keeps the transdermal pentamidine composition in a predefined space or reservoir (38) close to the skin (44).

Alternatively, the dose of the transdermal pentamidine composition to be administered can be applied from a dispenser to the occlusive covering (36) within the boundaries of the adhesive layer (40) depicted in FIG. 4. The then-formed transdermal patch can be applied to the skin of the patient to be treated. The methods of administration described with regard to FIGS. 3 and 4 are particularly advantageous because it permits dose titration to meet individual patient needs.

Figure 5:
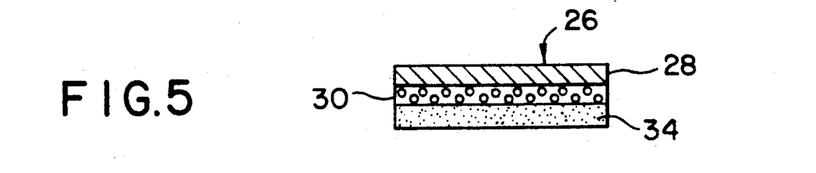

FIG. 5 illustrates another embodiment of a transdermal patch of the invention, generally designated as 26. The transdermal patch (26) includes a backing layer (28), a transdermal composition layer (30) and an adhesive layer (34). The backing layer and transdermal composition layer can have the same properties and are chosen for the reasons stated above. The adhesive layer can have the same properties as above and is chosen for the same reasons as above. Additionally, the adhesive layer (34) must be permeable to the transdermal composition and can not constitute a significant barrier to its passage. The transdermal patch (26) can also include a protective undercoating lamina (not shown). Prior to use the undercoating lamina is pulled away from the adhesive layer (34) and discarded to expose the adhesive layer. The undercoating lamina can be made from materials that are substantially impermeable to the pentamidine, the penetration enhancer and any other components of the transdermal composition layer and adhesive layer (30).

The transdermal patch of the invention can be applied to the skin of patients. The transdermal patch is positioned in firm contact with the patient's skin, preferably forming a tight seal therewith. The pentamidine in the patch migrates from the patch to the patient's skin by diffusion. When the pentamidine is in contact with the patient's skin, pentamidine molecules along the outer surface of the transdermal patch migrate through, and are absorbed by, the skin, entering the patient's circulation through the capillary network. The transdermal patch can be applied to any area of the patient's skin.

The following examples describe and illustrate the methods for the preparation of the pharmaceutical compositions of the present invention, and the results achieved thereby, in further detail. Both an explanation of, and the actual procedures for, the various aspects of the present invention are described where appropriate. These examples are intended to be merely illustrative of the present invention, and not limiting thereof in either scope or spirit. Those of skill in the art will readily understand that known variations of the conditions and processes of the preparative procedures described in these examples can be used to prepare the transdermal compositions and patches of the present invention.

EXAMPLE 1

| | | |
|---|---|---|
| Pentamidine isethionate | 100 mg/ml | (10.0%) |
| (−) Menthol | 20 mg/ml | (2.0%) |
| Lauric acid | 5 mg/ml | (0.5%) |
| Hydroxypropyl Cellulose (HPC), Aqualon Corp.'s KLUCEL, type HF/NF | 30 mg/ml | (3.0%) |
| 60% Isopropanol/40% water (IPA/H$_2$O) (final volume 1 ml) | 845 mg/ml | (84.5%) |

A gel was made by slow addition of the powdered HPC to a stirred solution of pentamidine isethionate, menthol, lauric acid and IPA/H$_2$O maintained at 65° to 75° C. The hot solution gelled within five to fifteen minutes and was poured while hot into a dispensing-measuring device (a syringe barrel, a sealable gel tube). The gel was allowed to cool to room temperature.

EXAMPLE 2

| | | |
|---|---|---|
| Pentamidine isethionate | 100 mg/ml | (10.0%) |
| (−) Menthol | 20 mg/ml | (2.0%) |
| Oleic acid | 5 mg/ml | (0.5%) |
| Vitamin E | 0.5 mg/ml | (0.05%) |
| HPC HF/NF | 30 mg/ml | (3.0%) |
| 60% Isopropanol/40% water | 844.5 mg/ml | (84.45%) | a gel was made in the same manner as Example 1 with substitution of oleic acid for the lauric acid and addition of Vitamin E as an antioxidant.

EXAMPLE 3

| | | |
|---|---|---|
| Pentamidine isethionate | 250.0 mg | (25.0%) |
| Menthol | 50.0 mg | (5.0%) |

-continued

| | | |
|---|---|---|
| Methyl Paraben | 1.0 mg | (0.1%) |
| Propyl Paraben | 0.5 mg | (0.05%) |
| IPA/Water (3:7 w/w) | 673.5 mg | (67.3%) |
| Carboxypolymethylene (Carbopol 940 from BF Goodrich) | 25.0 mg | (2.5%) |

The dry ingredients (pentamidine isethionate, menthol methyl and propyl paraben) were dissolved in the IPA/Water. To the resultant solution Carbopol 940 was gradually added with vigorous stirring. Gentle stirring was continued until the solution thickened ($\approx$ 15 minutes). This formulation was found to be efficacious in the Rabbit Irritation Study. The data is reported in Table XIV.

EXPERIMENTAL

In Vitro Experiments

The in vitro studies described herein measured the rate of pentamidine transport across skin excised from a "nude" mouse. The skin is placed in a vertical two-chambered device. The skin partitions between a donor compartment containing a formulation to be tested and a receptor compartment containing the aqueous medium. The skin is clamped in place with skin epidermis facing the donor compartment. A water jacket maintains a constant temperature (37° C.). The receptor compartment solution is constantly stirred and completely replaced with new solution at about the following time points during the assay: 2 hr, 5 hr, 7 hr, 24 hr and 29 hr.

Figure 8:
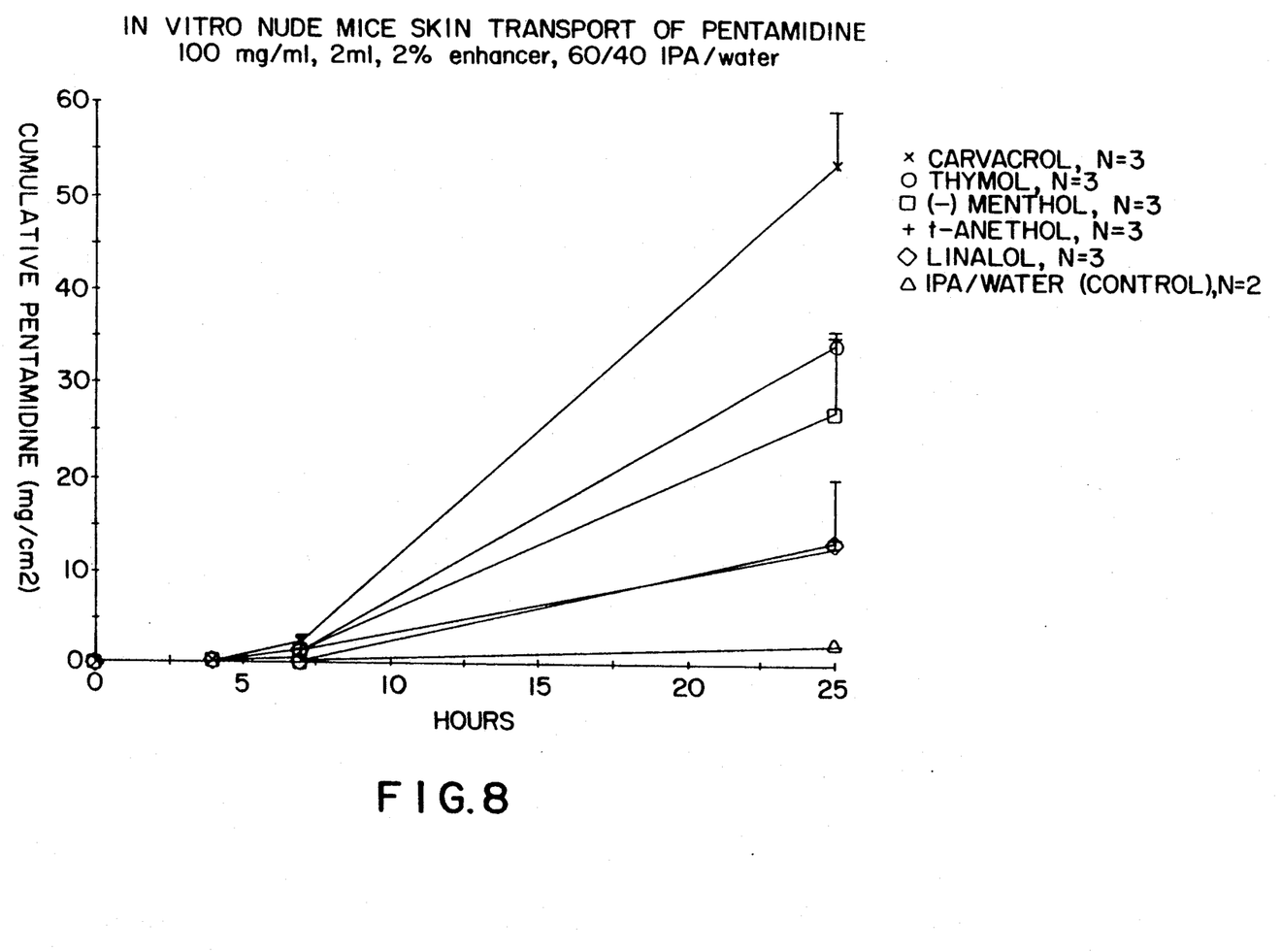

Tables I-VII and FIG. 8 show the results of the in vitro experiments using terpenes as penetration enhancers.

EXAMPLES 4-15

The following pharmaceutical formulations were prepared by using the procedure of Example 1 with the exception of compounds and concentrations as indicated in the following Table I.

TABLE I***

RATE OF TRANSPORT OF PENTAMIDINE IN VITRO

| Examples | Enhancer | Total mg./24 hr[1] | mg./hr* | Enhancement Factor** |
|---|---|---|---|---|
| 4 | none | 0.05 ± 0.003 | 0.003 | 1 |
| 5 | none | 0.11 ± 0.02 | 0.006 | 2 |
| 6 | 2% (−) menthol | 13.3 ± 2.6 | 0.771 | 257 |
| 7 | 5% (−) menthol | 15.7 ± 1.2 | 0.728 | 243 |
| 8 | 10% (−) menthol | 15.9 ± 0.2 | 0.622 | 207 |
| 9 | 2% (−) menthol | 10.8 ± 3.9 | 0.634 | 211 |
| 10 | 2% (+) menthol | 15.0 ± 2.3 | 0.882 | 294 |
| 11 | 5% (+) camphor | 3.8 ± 1.2 | 0.222 | 74 |
| 12 | 1% (+) carvone | 1.6 ± 0.4 | 0.0935 | 31 |
| 13 | 1% geraniol | 0.65 ± 0.40 | 0.038 | 13 |
| 14 | 1% isopulegol | 1.4 ± 0.7 | 0.128 | 43 |
| 15 | alpha-terpineol | 0.80 ± 0.68 | 0.046 | 15 |

*FLUX: For hours 7 through 24
**Enhancement Factor quantifies the degree of enhancement of pentamidine absorption through the skin when administered together with a penetration enhancer. An enhancement factor of one corresponds to the amount of pentamidine transported through the skin when administered with water. The Enhancement Factor is therefore determined by dividing the mg. of pentamidine transported across the skin per hour when administered with a terpene by the mg. of pentamidine transported across the skin per hour when administered with water.
***All compositions in this table are made with 5% w/w of pentamidine isethionate. All compositions in this table except for Example 4 use 60/40 v/v IPA · H$_2$O as the solvent. Example 4 used H$_2$O only.
[1](±) shall be defined as standard deviation in this table and the following tables.

EXAMPLES 16-62

The following pharmaceutical formulations were prepared by dissolving any dry ingredients (i.e. pentamidine isethionate, terpene, methyl paraben, propyl paraben) in the solvent (i.e. isopropyl alcohol/water or propylene glycol/water). To the resultant solution, the polymer (i.e. carboxypolymethylene, polyquaternium-10) when used (Examples 41-48), was gradually added with vigorous stirring. Gentle stirring was then continued for the next 15 minutes or until the solution thickened. When polyquaternium-10 is the polymer heating was required to make the formulation gel.

TABLE II*

TRANSPORT OF PENTAMIDINE IN VITRO USING VARIOUS ENHANCERS

| Example | Enhancer | Cumulative Transfer mg/cm$^2$/24 hr |
|---|---|---|
| 16 | 1% (+) neomenthol | 12.5 ± 1.1 |
| 17 | 1% (+) camphor | 0.7 ± 0.08 |
| 18 | 1% (+) pulegone | 0.7 ± 0.1 |
| 19 | 1% (−) menthone | 3.0 ± 2.0 |
| 20 | 1% terpene-4-ol | 3.2 ± 0.1 |
| 21 | 1% α-terpineol | 0.80 ± 0.68 |
| 22 | 1% (−) menthol | 10.4 |
| 23 | 1% (−) menthol | 2.6 ± 2.7 |
| 24 | 1% (+) menthol | 9.5 ± 4.5 |

*All compositions are 5% w/w pentamidine isethionate and use a solvent of 60% IPA 40% H$_2$O v/v.

TABLE III*

TRANSPORT OF PENTAMIDINE IN VITRO USING VARIOUS SOLVENTS

| Example | Enhancer | Solvent Concentration | Cumulative Transfer mg/cm$^2$/24 hr |
|---|---|---|---|
| 25 | 2% (−) menthol | 30% IPA:70% H$_2$O | 29.2 ± 0.5 |
| 26 | 2% (−) menthol | 60% IPA:40% H$_2$O | 24.5 ± 4.7 |
| 27 | 2% (−) menthol | 30% PG**:70% H$_2$O | 8.1 ± 0.6 |
| 28 | 2% (−) menthol | 60% PG:40% H$_2$O | 11.2 ± 0.4 |
| 29 | 2% (−) menthol | 90% PG:10% H$_2$O | 9.3 ± 0.2 |
| 30 | 2% (−) menthol | 90% IPA:10% H$_2$O | 34.4 ± 3.2 |
| 31 | 5% (−) menthol | 60% IPA:40% H$_2$O | 21.9 ± 1.5 |
| 32 | 5% (−) menthol | 60% PG:40% H$_2$O | 16.7 ± 24 |

*These formulations all contain 5% w/w pentamidine isethionate and 0.5% lauric acid as a stabilizer.
**Hereinafter PG shall be used to represent propylene glycol as the solvent.

TABLE IV*

TRANSPORT OF PENTAMIDINE IN VITRO USING VARIOUS CONCENTRATIONS OF PENTAMIDINE ISETHIONATE

| Example | Pentamidine Isethionate Concentration (% w/w) | Cumulative Transfer mg/cm$^2$/24 hr |
|---|---|---|
| 33 | 10% | 20.1 ± 5.3 |
| 34 | 15% | 18.9 ± 7.7 |
| 35 | 1.25% | 4.5 ± 0.6 |
| 36 | 2.5% | 8.6 ± 3.0 |
| 37 | 5.0% | 10.6 ± 0.4 |
| 38 | 10.0% | 14.9 ± 3.0 |
| 39 | 10.0% | 20.0 ± 6.3 |
| 40 | 15.0% | 19.0 ± 7.7 |

*These formulations all contain 2% w/w of the penetration enhancer (−) menthol and a solvent composed of 60% IPA:40% H$_2$O v/v.

TABLE V*
TRANSPORT OF PENTAMIDINE IN VITRO WITH VARIOUS POLYMERS

| Example | Polymer | Polymer Conc. | Cumulative Transfer mg/cm$^2$/24 hr |
|---|---|---|---|
| 41 | [1]JR30M | 3% w/w | 5.85 ± 0.72 |
| 42 | [2]Kollidon 90 | 20% w/w | 1.84 ± 0.81 |
| 43 | Polyvinyl Alcohol | 20% w/w | 4.74 ± 0.04 |
| 44 | [3]Carbopol 934 | 3% w/w | 6.70 ± 0 |
| 45 | [3]Carbopol 940 | 3% w/w | 6.70 ± 0.71 |
| 46 | [3]Carbopol 1342 | 3% w/w | 5.65 ± 0.85 |
| 47 | Hydroxypropyl Cellulose | 3% w/w | 4.68 ± 0.66 |
| 48 | None | None | 7.13 ± 0.98 |

*These formulations all contain pentamidine isethionate in an amount of 10% w/w, 5% w/w (−) menthol, 0.1% allantoin, 0.1% methyl paraben, 0.05% propyl paraben and a solvent concentration of 50:50 v/v IPA:H$_2$O.
[1]Generically known as polyquaternium-10, commercially available from Union Carbide.
[2]Generically known as povidone, commercially available from BASF.
[3]Generically known as carboxy polymethylene, commercially available from BF Goodrich.

TABLE VI*
TRANSPORT OF PENTAMIDINE IN VITRO USING VARIOUS TERPENES

| Example | Terpene | Terpene Conc. | Cumulative Transfer mg/cm$^2$/24 hr |
|---|---|---|---|
| 49 | dihydrocarvone | 1% w/w | 1.35 ± 0.92 |
| 50 | carvone | 1% w/w | 0.72 ± 0.56 |
| 51 | carveol | 1% w/w | 1.13 ± 1.22 |
| 52 | dihydrocarveol | 1% w/w | 2.76 ± 3.88 |
| 53 | (−) menthol | 2% w/w | 11.71 ± 3.50 |
| 54 | (−) menthol | 1% w/w | 10.88 ± 1.28 |
| 55 | (−) menthol | 0.5 w/w | 10.36 ± 2.74 |

*These formulations all contain 5% w/w pentamidine isethionate, and a solvent of 60:40 v/v IPA · H$_2$O.

TABLE VII*
TRANSPORT OF PENTAMIDINE IN VITRO WITH VARIOUS TERPENES

| Example | Enhancer | Cumulative Transfer mg/cm$^2$/24 hr |
|---|---|---|
| 56 | 2% w/v carvacrol | 52.6 ± 5.5 |
| 57 | 2% w/v thymol | 33.0 ± 0.9 |
| 58 | 2% w/v t-anethole | 11.7 ± 0.8 |
| 59 | 2% w/v linalol | 12.3 ± 6.8 |
| 60 | 2% w/v citral | 5.0 ± 1.8 |
| 61 | 2% w/v l-menthol | 25.8 ± 8.7 |
| 62 | None | 0.93 ± 0.08 |

*All compositions contain 10% w/v pentamidine isethionate and 60/40 IPA · H$_2$O v/v as solvent.

In Vivo Experiments

Pentamidine was administered to four Rhesus monkeys by an IV infusion of 1 hr duration which was designed to deliver 4 mg drug/kg animal weight. Urine samples were obtained at −24 to 0 hr, 0 to 3 hr, 3 to 7 hr, 7 to 24 hr and 24 to 48 hr. Blood (2 ml) was withdrawn from an arm vein at −24 hr, 0.5 hr, 1 hr, 2 hr, 3 hr, 5 hr, 7 hr, 24 hr and 48 hr after the end of the IV infusion. Plasma was obtained from the heparinized blood by centrifugation.

A second monkey experiment evaluated transdermal delivery of pentamidine and utilized the same four monkeys that had been used for the IV infusion experiment but 8 weeks later. Hilltop Chambers (19 mm), filled with 18.2 mg. pentamidine (0.2 ml formulation), were applied to each of 16 positions on the chest of the monkey. The chest was cleared of hair by electric shaving the previous day. The bio-adhesive tape anchoring the polypropylene chambers containing the formulation was further secured by wrapping with hypoallergenic knitted tape. Five control patches, without pentamidine, containing isopropyl alcohol (IPA) solutions of either menthol, or lauric acid or both, were also applied. Time points similar to the IV infusion were taken. Urine and plasma samples from both experiments were assayed for pentamidine quantitation. The transdermal chambers were removed 24 hr after application and were analyzed for residual pentamidine. Only small amounts of the original dose of pentamidine were recovered. The data demonstrates that the pentamidine had been transported transdermally.

Figure 6:
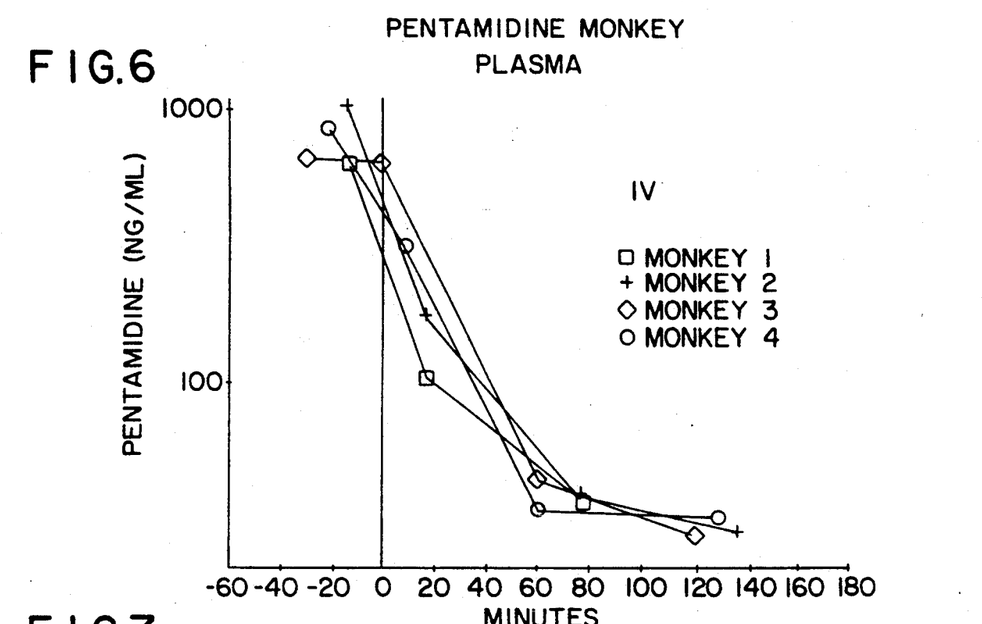
Figure 7:
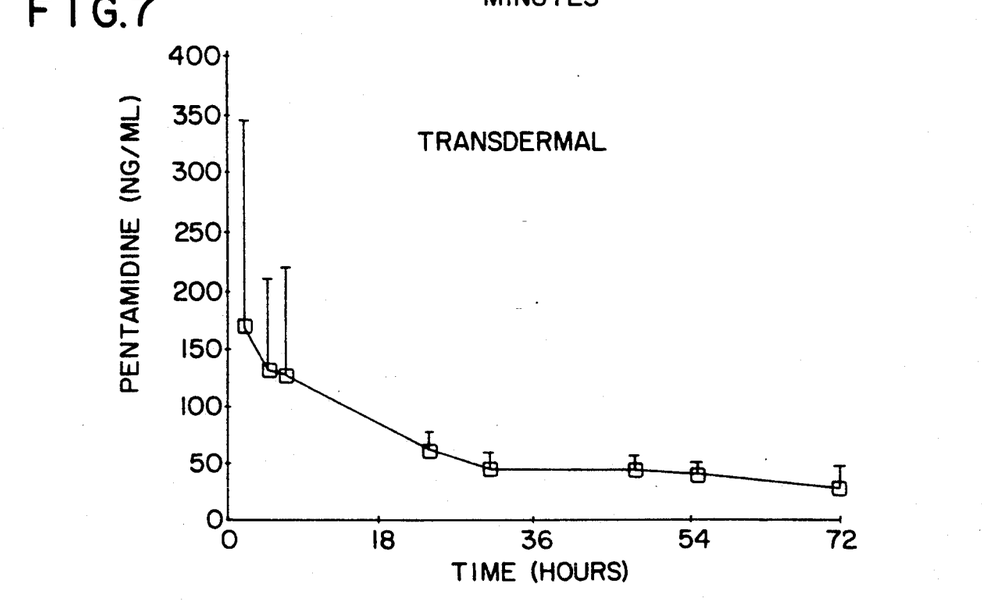

The following Tables VIII–X and FIG. 6 and FIG. 7 show the results of the in vivo experiments. This data demonstrates that effective blood levels of pentamidine can be achieved by transdermal delivery and that the terpenes increase penetration of pentamidine through the skin.

TABLE VIII

EXPERIMENTAL CONDITIONS FOR THE IV AND TRANSDERMAL DELIVERY OF PENTAMIDINE IN THE RHESUS MONKEYS

| | Monkey 1 | 2 | 3 | 4 |
|---|---|---|---|---|
| Weight, IV (kg) | 4.2 | 4.4 | 4.5 | 3.8 |
| Weight, trans (kg) | 4.2 | 4.5 | 4.5 | 3.6 |
| Total dose, IV (mg) | 16.8 | 7.4 | 18.0 | 15.2 |
| Total dose, Trans. (mg) | 292 | 292 | 292 | 292 |
| Dose, IV, (mg/kg) | 4 | 4 | 4 | 4 |
| Dose, trans. (mg/kg) | 69.5 | 65.6 | 64.9 | 82.3 |

TABLE IX

PHARMACOKINETIC PARAMETERS CALCULATED FROM THE IV AND TRANSDERMAL PLASMA LEVELS OF PENTAMIDINE

| | Monkey 1 | 2 | 3 | 4 | Average (SD) |
|---|---|---|---|---|---|
| AUC, IV (0–5 h) (ng/ml) h | 428 | 719 | 883 | 784 | 704 (196) |
| AUC, Trans (0–72 hr) (ng/ml) h | 7407 | 3426 | 2721 | 4384 | 4485 (2064) |
| % Absolute Bioavail.[1] | 99.2 | 29.03 | 18.99 | 27.19 | 43.6 (37.3) |
| Total Clearance, IV dose lt/h[2] | 39.27 | 24.18 | 20.38 | 19.38 | 25.8 (9.21) |
| Renal Clearance, IV dose lt/h[3] | 0.840 | 0.96 | 0.54 | 0.069 | 0.60 (0.40) |

[1]% AB = (AUCtrans/AUCiv) × (DOSEiv/DOSEtrans) × 100
[2]Total Clearance - DOSEiv/AUCiv
[3]Renal Clearance = Amount in urine (0–48 h)/AUCiv

TABLE X

PHARMACOKINETIC PARAMETERS CALCULATED FROM THE URINE DATA FOLLOWING IV AND TRANSDERMAL APPLICATION OF PENTAMIDINE

| | Monkey 1 | 2 | 3 | 4 | Average (SD) |
|---|---|---|---|---|---|
| Urine Cum. Pentam., IV 0–48 h, (mg) | 0.360 | 0.691 | 0.473 | 0.054 | 0.39 (0.27) |
| Urine Cum. Pentam., Trans. 0–48 h, (mg) | 3.16 | 2.18 | 5.61 | 0.95 | 2.98 (1.97) |
| % Bioavailability[1] | 50.34 | 19.32 | 73.28 | 85.62 | 57.1 (29.1) |
| % Absorbed (from residual analysis in the pads) | 70.9 | 54.4 | 58.8 | 46.5 | 57.7 (10.2) |
| % Dose excreted in urine, | 2.14 | 3.89 | 2.63 | 0.36 | 2.28 (1.49) |

TABLE X-continued

PHARMACOKINETIC PARAMETERS CALCULATED FROM THE URINE DATA FOLLOWING IV AND TRANSDERMAL APPLICATION OF PENTAMIDINE

| | Monkey | | | | |
|---|---|---|---|---|---|
| | 1 | 2 | 3 | 4 | Average (SD) |
| IV dose 0–48 h | | | | | |
| % Dose absorbed excreted in urine, transdermal dose 0–48[2] | 2.15 | 3.88 | 2.62 | 0.38 | 2.26 (1.45) |

[1]The % bioavailability was obtained from the ratio of the total pentamidine excreted in urine following IV and transdermal routes. The ratio was corrected for the dose.
[2]% bioavailability from the urine data was used to obtain the % of the dose absorbed.

RABBIT IRRITATION/DELIVERY FORMULATION SCREENING

To measure delivery using residual analysis and skin irritation concurrently the backs of New Zealand white rabbits were shaven 24 hours prior to formulation application. Each gel formulation (0.2 ml) was placed into a Hilltop chamber and secured onto back of the rabbit with Dermiform knitted tape. After all formulations were applied, the area was wrapped with Coban elastic wrap. At the designated study time, usually 24 hours, the chambers were removed, and the residual gel was placed into a polypropylene container. To remove any remaining formulation, the application area was wiped with an alcohol swab. These swabs were extracted with 100 ml of isopropanol-water (60:40, v/v) and the residual pentamidine was analyzed by reverse-phase HPLC with fluorescence detection. The amount of drug delivered from each formulation was calculated from this analysis. Irritation was monitored at 24 and 72 hours. The combined scoring for redness and edema resulted in the Draize score. The results of the studies are reported in Tables XI–XIV.

The following is the scoring criteria for dermal reactions*

| Score | Erythema and Eschar Formation |
|---|---|
| 0 | No erythema |
| 1 | Very slight erythema (barely perceptible, edges of area not well defined) |
| 2 | Slight erythema (pale red in color, edges definable) |
| 3 | Moderate to severe erythema (definite red in color, area well defined) |
| 4 | Severe erythema (beet or crimson red) to slight eschar formation (injuries in depth) |
| 4 | TOTAL ERYTHEMA SCORE POSSIBLE (per site) |

| Score | Edema Formation |
|---|---|
| 0 | No edema |
| 1 | Very slight edema (barely perceptible, edges of area not well defined) |
| 2 | Slight edema (edges of area well defined by definite raising) |
| 3 | Moderate edema (area raised approximately 1 mm) |
| 4 | Severe edema (area raised more than 1 mm and extending beyond the area of exposure) |
| 4 | TOTAL EDEMA SCORE POSSIBLE (per site) |
| 8 | TOTAL PRIMARY IRRITATION SCORE POSSIBLE (per site) (Erythema + Edema) |

| DESCRIPTIVE CLASSIFICATION Mean Primary Dermal Irritation Index | |
|---|---|
| Range of Values | Descriptive Classification |
| 0 | Non-irritating |
| 0.1–1.9 | Mildly irritating |
| 2.0–5.9 | Moderately irritating |
| 6.0–8.0 | Severely Irritating |

*Draize, J. H., 1965. The Appraisal of the Safety of Chemicals in Food, Drugs and Cosmetics. Dermal Toxicity, pp. 46–59. Assoc. of Food and Drug Officials of the U.S., Topeka, Kans.

EXAMPLES 63–111

The following formulations 63–111 were prepared as in Examples 16–62 with the exception of varying concentrations and compounds used.

TABLE XI

Rabbit Residual Analysis and Skin Irritation Results*

| Example | Pentamidine % w/w | Enhancer % w/w | Fatty Acid % w/w | mg transferred | 24 hr irritation | 72 hr irritation |
|---|---|---|---|---|---|---|
| 63 | 10% | 2% (−) menthol | — | 7.34 ± 1.90 | 1.83 ± 0.41 | 1.83 ± 1.94 |
| 64 | 10% | 10% (−) menthol | — | 15.97 ± 0.53 | 6.5 ± 2.07 | 5.0 ± 0.63 |
| 65 | 10% | 2% (−) menthol | 0.5% Oleic Acid | 0.68 ± 2.41 | 1.67 ± 1.51 | 1.33 ± 1.03 |
| 66 | 10% | 2% (−) menthol | 0.5% Lauric Acid | 8.42 ± 1.93 | 1.83 ± 0.98 | 2.83 ± 2.14 |
| 67 | 10% | 10% (−) menthol | 0.5% Lauric Acid | 15.75 ± 0.69 | 6.33 ± 2.58 | 4.83 ± 0.41 |
| 68 | 10% | 5% (−) menthol | 0.5% Lauric Acid | 13.41 ± 2.3 | 5.67 ± 2.58 | 4.83 ± 1.17 |
| 69 | 10% | 2% (−) menthol | 1% Lauric Acid | 7.66 ± 2.48 | 2.33 ± 1.86 | 3.33 ± 1.86 |
| 70 | 2.5% | 2% (−) menthol | — | 7.39 ± 1.58 | 1.67 ± 1.86 | 2.67 ± 2.25 |
| 71 | 2.5% | 2% (−) menthol | 1% Lauric Acid | 7.51 ± 2.78 | 2.0 ± 1.26 | 3.67 ± 2.25 |
| 72 | 2.5% | none | 1% Lauric Acid | 7.15 ± 2.85 | 1.67 ± 1.51 | 2.33 ± 1.97 |

*All formulations contain 3% w/w hydroxypropylcellulose (HPC) and 60:40 (w:w) IPA · H₂O

TABLE XII

Rabbit Residual Analysis and Skin Irritation Results*

| Example | Pentamidine % w/w | Enhancer % w/w | Solvent (IPA:H2O) | Hours Pad On | mg transferred | 24 hr irritation | 72 hr irritation |
|---|---|---|---|---|---|---|---|
| 73 | 15 | 5% (−) menthol | 40:60 | 4 | 15.77 ± 2.52 | 1 ± 1.41 | 1.25 ± 1.89 |
| 74 | 15 | 5% (−) menthol | 40:60 | 8 | 19.35 ± 3.28 | 0.25 ± 0.5 | 1.50 ± 1.29 |
| 75 | 15 | 5% (−) menthol | 40:60 | 12 | 15.09 ± 3.40 | 1.00 ± 0.82 | 0.25 ± 0.50 |
| 76 | 15 | 5% (−) menthol | 40:60 | 24 | 16.65 ± 1.30 | 1.00 ± 0.82 | 1.50 ± 1.29 |
| 77 | 10 | 2% (−) menthol | 60:40 | 4 | 4.97 ± 4.36 | 0.50 ± 1.00 | 0.25 ± 0.50 |
| 78 | 10 | 2% (−) menthol | 60:40 | 8 | 4.95 ± 0.43 | 0 ± 0 | 0.25 ± 0.50 |
| 79 | 10 | 2% (−) menthol | 60:40 | 12 | 5.16 ± 4.27 | 1.50 ± 1.29 | 0.25 ± 0.50 |
| 80 | 10 | 2% (−) menthol | 60:40 | 24 | 6.76 ± 3.53 | 0.50 ± 0.58 | 0.75 ± 0.50 |
| 81 | 10 | 5% (−) menthol | 60:40 | 4 | 5.38 ± 3.31 | 1.50 ± 1.73 | 1.50 ± 1.29 |
| 82 | 10 | 5% (−) menthol | 60:40 | 8 | 5.97 ± 1.78 | 1.50 ± 1.29 | 1.75 ± 1.50 |

TABLE XII-continued

Rabbit Residual Analysis and Skin Irritation Results*

| Example | Pentamidine % w/w | Enhancer % w/w | Solvent (IPA:H2O) | Hours Pad On | mg transferred | 24 hr irritation | 72 hr irritation |
|---|---|---|---|---|---|---|---|
| 83 | 10 | 5% (−) menthol | 60:40 | 12 | 4.85 ± 1.80 | 2.75 ± 1.71 | 2.00 ± 1.41 |
| 84 | 10 | 5% (−) menthol | 60:40 | 24 | 8.85 ± 2.27 | 4.25 ± 0.96 | 4.25 ± 0.76 |
| 85 | 10 | 10% (−) menthol | 60:40 | 4 | 8.83 ± 0.34 | 3.50 ± 0.58 | 4.00 ± 0.00 |
| 86 | 10 | 10% (−) menthol | 60:40 | 8 | 9.88 ± 1.88 | 3.25 ± 0.96 | 3.00 ± 0.82 |
| 87 | 10 | 10% (−) menthol | 60:40 | 12 | 13.79 ± 0.68 | 4.50 ± 0.58 | 3.75 ± 1.87 |
| 88 | 10 | 10% (−) menthol | 60:40 | 24 | 14.35 ± 0.86 | 4.75 ± 0.50 | 5.75 ± 0.50 |

*All formulations contain 3% hydroxypropylcellulose

TABLE XIII

Rabbit Residual and Skin Irritation Results*

| Example | Pentamidine Conc. w/w % | Polymer Conc. w/w % | Enhancer Conc. w/w % | IPA:H2O Solvent Conc. w/w % | mg transferred | 24 hr irritation | 72 hr irritation |
|---|---|---|---|---|---|---|---|
| 89 | 10% | none | 5% menthol | 50:50 | 13.83 ± .76 | 2.5 ± 1.29 | 4.25 ± 1.71 |
| 90 | 10% | 3% | 5% menthol | 50:50 | 15.27 ± .96 | 2.0 ± 1.41 | 4.5 ± 0.58 |
| 91 | 15% | 3% | 3% menthol | 50:50 | 9.8 ± 1.0 | 2.5 ± 1.29 | 2.75 ± 2.75 |
| 92 | 20% | 3% | 2% menthol | 50:50 | 10.16 ± 3.22 | 2.25 ± 1.71 | 1.0 ± 0.82 |
| 93 | 15% | 2% | 3% menthol | 50:50 | 11.82 ± 1.01 | 2.25 ± 2.63 | 3.0 ± 2.16 |
| 94 | 15% | 4.5% | 3% menthol | 50:50 | 12.2 ± 1.49 | 2.5 ± 1.0 | 2.5 ± 1.73 |
| 95 | 15% | 3% | 3% menthol | 40:60 | 9.16 ± 3.41 | 0.25 ± 0.5 | 1.0 ± 1.15 |
| 96 | 15% | 3% | 3% menthol | 60:40 | 10.39 ± 2.94 | 2.75 ± 1.26 | 2.75 ± 2.5 |
| 97 | 10% | none | 5% menthol | 50:50 | 13.47 ± 0.89 | 1.50 ± 1.73 | 4.5 ± 1.73 |

*All formulations contain Carbopol 1342 as the polymer, 0.1% allantoin, 0.1% methyl paraben and 0.05% propyl paraben.

TABLE XIV

Rabbit Residual and Skin Irritation Results*

| Example | Pentamidine Conc. w/w % | Polymer Conc. w/w % | Enhancer Conc. w/w % | IPA:H2O Solvent Conc. | mg transferred | 24 hr irritation | 72 hr irritation |
|---|---|---|---|---|---|---|---|
| 98 | 20% | 2.5% | 5% menthol | 40:60 | 23.14 ± 3.32 | 2.25 ± 1.26 | 2.5 ± 0.58 |
| 99 | 20% | 2.5% | 5% menthol | 30:70 | 23.67 ± 9.14 | 1.5 ± 0.58 | 1.0 ± 1.41 |
| 100 | 20% | 2.5 | 5% menthol | 20:80 | 24.31 ± 11.84 | 1.75 ± 0.96 | 0.75 ± 0.96 |
| 101 | 10% | none | 5% menthol | 60:40 | 13.99 ± 2.98 | 1.75 ± 2.06 | 3.0 ± 1.15 |
| 3 | 25% | 2.5% | 5% menthol | 30:70 | 36.28 ± 9.66 | 1.0 ± 0.82 | 2.0 ± 1.83 |
| 3*** | 25% | 2.5% | 5% menthol | 30:70 | 27.17 ± 6.54 | 2.75 ± 0.5 | 2.5 ± 1.91 |
| 103 | 15% | 2.5% | 5% menthol | 30:70 | 23.33 ± 4.73 | 1.5 ± 0.58 | 1.0 ± 0.82 |
| 104 | 20% | 2.5% | 5% menthol | 30:70 | 23.64 ± 13.22 | 1.25 ± 0.5 | 1.0 ± 1.41 |
| 105 | 20% | 2.5% | 5% menthol | 30:70 | 28.76 ± 4.03 | 2.0 ± 1.15 | 2.75 ± 2.06 |
| 106 | 20% | 2.5% | 10% menthol | 30:70 | 24.86 ± 6.83 | 1.75 ± 0.5 | 1.5 ± 1.29 |
| 107 | 25% | 2.0% | 5% menthol | 30:70 | 29.14 ± 9.88 | 2.25 ± 0.5 | 1.25 ± 0.5 |
| 108** | 25% | 2% | 5% menthol | 30:70 | 33.65 ± 8.81 | 2.25 ± 0.96 | 2.0 ± 1.41 |
| 109 | none | 2% | 5% menthol | 30:70 | — | 3.25 ± 1.50 | 3.0 ± 2.0 |
| 110 | 25% | 2% | 5% menthol | 20:80 | 36.1 ± 5.96 | 3.5 ± 0.58 | 3.25 ± 1.71 |
| 111 | 25% | 2% | 4% menthol | 30:70 | 31.67 ± 6.75 | 2.75 ± 1.26 | 3.25 ± 1.71 |

*All formulations contain Carbopol 940, 0.1% allantoin, 0.1% methyl paraben and 0.05% propyl paraben.
**All pads were applied for 4 hour periods with the exception of Example 108 which was applied for 7 hours.
***This formulation was two weeks old in order to show the effect of aging on the composition.

The transdermal compositions and transdermal patches according to the present invention are advantageous in that they offer: ease of application; decreased risk to healthcare workers of exposure to pentamidine; prevention of systemic infections; an efficient dose form for the pediatric group; and minimized side effects when compared to other forms of administration of pentamidine.

What is claimed is:

1. A pharmaceutical composition for transdermal delivery of pentamidine or a pharmaceutically acceptable salt of pentamidine comprising:
   a therapeutically effective amount of pentamidine or a pharmaceutically acceptable salt of pentamidine;
   a penetration enhancing amount of a terpene selected from the group consisting of menthol, carveol, dihydrocarveol, dihydrocarvone, carvone, neomenthol, isopulegol, camphor, pulegone, geraniol, α-terpineol, terpene-4-ol, menthone, linalol, carvacrol, thymol, citral and t-anethole for delivering a therapeutically effective amount of pentamidine through the skin; and
   a pharmaceutically acceptable carrier.

2. A composition according to claim 1 wherein the terpene is selected from the group consisting of (±)-menthol, (−)-menthol and (+)-menthol.

3. A composition according to claim 2 wherein the penetration enhancing amount of the terpene comprises from 2–10% by weight of the composition.

4. A composition according to claim 3 wherein the penetration enhancing amount of the terpene comprises 5% by weight of the composition.

5. A composition according to claim 4 wherein the terpene comprises (±)-menthol.

6. A composition according to claim 4 wherein the terpene comprises (−)-menthol.

7. A composition according to claim 4 wherein the terpene comprises (+)-menthol.

8. A composition according to claim 1 wherein the therapeutically effective amount of pentamidine comprises 25% by weight of the composition.

9. A composition according to claim 1 wherein the pharmaceutical carrier comprises a mixture of isopropanol and water.

10. A pharmaceutical composition for transdermal delivery of pentamidine or a pharmaceutically acceptable salt of pentamidine comprising:
   a therapeutically effective amount of pentamidine or a pharmaceutically acceptable salt of pentamidine;
   a penetration enhancing amount of a terpene selected from the group consisting of (−)-menthol, (+)-menthol and (±)-menthol for delivering a therapeutically effective amount of pentamidine through the skin; and
   a pharmaceutically acceptable carrier.

11. A composition according to claim 10 wherein the therapeutically effective amount of pentamidine comprises from 10 to 25% by weight and the penetration enhancing amount of terpene comprises from 2 to 10% by weight of the composition.

12. A composition according to claim 11 wherein the penetration enhancing amount of terpene comprises by weight of the composition.

13. A composition according to claim 12 wherein the terpene comprises (±)-menthol.

14. A composition according to claim 12 wherein the terpene comprises (−)-menthol.

15. A composition according to claim 12 wherein the terpene comprises (+)-menthol.

16. In a transdermal patch having a backing layer and a reservoir or matrix containing a pharmaceutical composition for transdermal delivery of the pharmaceutical composition the improvement comprising a pharmaceutical composition comprised of:
   a therapeutically effective amount of pentamidine or a pharmaceutically acceptable salt of pentamidine; and
   a penetration enhancing amount of a terpene selected from the group consisting of menthol, carvone, carveol, dihydrocarveol, dihydrocarvone, neomenthol, isopulegol, pulegol, camphor, geraniol, α-terpineol, terpene-4-ol, menthone, linalol, carvacrol, thymol, citral and t-anethole for delivering a therapeutically effective amount of pentamidine through the skin.

17. A transdermal patch according to claim 16 wherein the terpene is selected from the group consisting of (±)-menthol, (−)menthol and (+)-menthol.

18. A transdermal patch according to claim 16 wherein the penetration enhancing amount of the terpene comprises from 2-10% by weight of the composition.

19. A transdermal patch according to claim 18 wherein the penetration enhancing amount of the terpene comprises 5% by weight of the composition.

20. A transdermal patch according to claim 19 wherein the terpene comprises (±)-menthol.

21. A transdermal patch according to claim 19 wherein the terpene comprises (+)-menthol.

22. A transdermal patch according to claim 19 wherein the terpene comprises (−)-menthol.

23. A transdermal patch according to claim 19 wherein the therapeutically effective amount of pentamidine comprises 25% by weight of the composition.

24. A method for transdermal delivery of pentamidine or a pharmaceutically acceptable salt, comprising: administering a pharmaceutical composition comprising:
   a therapeutically effective amount of pentamidine or a pharmaceutically acceptable salt of pentamidine;
   a penetration enhancing amount of terpene selected from the group consisting of menthol, carvone, carveol, dihydrocarveol, dihydrocarvone, neomenthol, isopulegol, camphor, pulegone, geraniol, α-terpineol, terpene-4-ol, menthone, linalol, citral, carvacrol, thymol and t-anethole for delivering a therapeutically effective amount of pentamidine through the skin; and
   a pharmaceutically acceptable carrier.

25. A method according to claim 24 wherein the terpene is selected from the group consisting of (±)-menthol, (−)-menthol and (+)-menthol.

26. A method according to claim 25 wherein the penetration enhancing amount of terpene comprises from 2-10% by weight of the composition.

27. A method according to claim 26 wherein the penetration enhancing amount of terpene comprises 5% by weight of the composition.

28. A method according to claim 27 wherein the terpene comprises (±)-menthol.

29. A method according to claim 27 wherein the terpene comprises (−)-menthol.

30. A method according to claim 27 wherein the terpene comprises (+)-menthol.

* * * * *

UNITED STATES PATENT AND TRADEMARK OFFICE
CERTIFICATE OF CORRECTION

PATENT NO. : 5,230,897
DATED : July 27, 1993
INVENTOR(S) : Griffin, et al.

It is certified that error appears in the above-indentified patent and that said Letters Patent is hereby corrected as shown below:

Column 4, line 7, reading "such a 50%" should read -- such as 50% --.

Column 8, line 61, reading "a gel was" should read -- A gel was --.

Column 9, line 10, reading "menthol methyl" should read -- menthol, methyl --.

Column 12, line 28, reading "7.4" should read -- 17.4 --.

Column 17, line 21, reading "comprises by" should read -- comprises 5% by --.

Signed and Sealed this

Twenty-second Day of November, 1994

Attest:

BRUCE LEHMAN

*Attesting Officer*     *Commissioner of Patents and Trademarks*